(12) United States Patent
Rugfelt

(10) Patent No.: US 7,273,462 B2
(45) Date of Patent: Sep. 25, 2007

(54) DEVICE FOR SUPPORTING AND STABILIZING AN INJURED PERSON OR INJURED BODY PART AND METHOD FOR PRODUCING THE DEVICE

(75) Inventor: Hakan Rugfelt, Falsterbo (SE)

(73) Assignee: Kohlbrat & Bunz Gesellschaft m.b.H., Radstadt (AT)

( * ) Notice: Subject to any disclaimer, the term of this patent is extended or adjusted under 35 U.S.C. 154(b) by 373 days.

(21) Appl. No.: 11/032,484

(22) Filed: Jan. 10, 2005

(65) Prior Publication Data

US 2005/0137513 A1   Jun. 23, 2005

Related U.S. Application Data

(63) Continuation of application No. PCT/AT03/00190, filed on Jul. 8, 2003.

(30) Foreign Application Priority Data

Jul. 9, 2002   (AT) ................. A 1029/2002

(51) Int. Cl.
*A61F 5/00*   (2006.01)
*A61G 15/00*   (2006.01)

(52) U.S. Cl. .................. 602/5; 128/845; 128/846; 128/869

(58) Field of Classification Search ............. 128/845, 128/846, 869, 870; 602/5, 13, 18
See application file for complete search history.

(56) References Cited

U.S. PATENT DOCUMENTS

| | | |
|---|---|---|
| 3,745,998 A | 7/1973 | Rose |
| 4,301,791 A | 11/1981 | Franco, III |
| 4,657,003 A | 4/1987 | Wirtz |
| 4,788,972 A | 12/1988 | DeBusk |
| 5,154,185 A | 10/1992 | Latimer et al. |
| 5,720,058 A | 2/1998 | Hollander et al. |
| 5,887,299 A | 3/1999 | Phillips |
| 6,152,952 A | 11/2000 | Owens |
| 2003/0139694 A1 | 7/2003 | Rugfelt et al. |

FOREIGN PATENT DOCUMENTS

| | | |
|---|---|---|
| CH | 661 204 A5 | 7/1987 |
| CH | 675 066 A5 | 8/1990 |
| EP | 0 267 640 A1 | 5/1988 |
| EP | 0 432 330 A1 | 6/1991 |
| EP | 0 712 595 A1 | 5/1996 |
| EP | 0 903 129 A1 | 3/1999 |
| NL | 7101392 | 8/1972 |
| WO | 94/10946 | 5/1994 |
| WO | 01/30280 A1 | 5/2001 |

*Primary Examiner*—Kim M Lewis
(74) *Attorney, Agent, or Firm*—Laurence A. Greenberg; Werner H. Stemer; Ralph E. Locher

(57) ABSTRACT

An injured person or an injured limb is supported and stabilized with a flexible film element enclosing an airtight inner region that can be evacuated. The film element is provided with two insertion bodies which respectively are formed with two air-permeable, flexible material strips. Each insertion body is divided into chambers containing loose particles, by way of intersecting seams formed between the material strips. The seams on both insertion bodies are staggered in relation to each other in both directions in such a way that the particles combine to form a substantially homogeneously thick particle layer.

5 Claims, 2 Drawing Sheets

DEVICE FOR SUPPORTING AND STABILIZING AN INJURED PERSON OR INJURED BODY PART AND METHOD FOR PRODUCING THE DEVICE

CROSS-REFERENCE TO RELATED APPLICATION

This is a continuing application, under 35 U.S.C. § 120, of copending international application No. PCT/AT2003/000190, filed Jul. 8, 2003, which designated the United States; this application also claims the priority, under 35 U.S.C. § 119, of German patent application No. A 1029/2002, filed Jul. 9, 2002; the prior applications are herewith incorporated by reference in their entirety.

BACKGROUND OF THE INVENTION

Field of the Invention

The invention relates to a device for supporting and stabilizing an injured person or injured body part. The device has a flexible film element which can be secured around the injured person or the body part and encloses an airtight evacuable inner space in which two insert bodies are provided. The insert bodies are each formed from two air-permeable, flexible lengths of material, each insert body being divided by a plurality of parallel seams between the lengths of material into chambers which contain loose particles. The seams on the two insert bodies are offset with respect to one another in such a manner that the particles complement one another to form a substantially uniformly thick layer of particles. The invention further pertains to a method for producing an insert body.

Rescue and transportation configurations referred to as vacuum mattresses, vacuum jackets, and vacuum splints have a casing made of an airtight plastic film and a filling consisting of plastic granules, in particular of foamed polystyrene beads, and, after they have been fitted and fixed to an injured person or injured body part that is to be stabilized, they can be evacuated by means of a suction pump. This leads to a tight packing of the granule filling and therefore to a stiffening of the flexible element which thereby forms a substantially rigid casing or sleeve round the body part.

A configuration of that type is disclosed in the commonly assigned, published international patent publication WO 01/30280 (corresponding to U.S. Patent Application Publication U.S. 2003/0139694 A1). In one embodiment, we show a division of the inner space into five compartments by means of four air-permeable lengths of material, the particle-containing chambers being provided in the second compartment and in the fourth compartment. For this purpose, the lengths of material are connected in pairs to one another by means of parallel connecting seams, each connecting seam of two lengths of material being offset in each case by half the width of the chamber with respect to a connecting seam of the two other lengths of material, so that the two rows of chambers overlap each other and a connecting seam is situated in each case in the region of an apex of a chamber. In spite of particles being absent in the region of the connecting seams, the overlapping of the chambers leads to a virtually uniform distribution of the filling since, with the inner space evacuated, the particles of adjacent chambers complement one another to form an essentially uniform layer. In the production of this embodiment, first of all two insert bodies composed of two lengths of material in each case are produced and are filled with the particles. The insert bodies are then fastened in each case along their periphery in the edge region of a film, and the two films are finally connected along their edges.

The configuration according to WO 01/30280 and U.S. 2003/0139694 A1 is primarily designed as an upper-body supporting and stabilizing jacket, in the insert bodies of which the chambers run in the circumferential direction, i.e. horizontally around the upper body in the seated position. The mobility of the particles is reduced in the longitudinal direction of the chambers only by the small width of the chambers. Nevertheless, it is generally necessary to distribute the particles by hand with all due care and attention before the arrangement is put onto the injured person, which takes time. In the evacuated state, the stability of the device is good in the longitudinal direction of the chambers, but is poorer in the longitudinal direction of the injured person, since the packing of the particles is often interrupted by the cross pieces which form buckling zones.

Swiss patent CH 661 204 shows a stabilizing device for the entire body, the chambers of which device run in the direction of the spinal column. The above-described disadvantages therefore occur offset in each case by 90°. During handling, the loose particles slide into the head or foot region, and the transverse stability is poorer. Added to this is a further effect which is disadvantageous for the injured person, namely the considerable shrinkage in length, in the centimeter range, during the evacuation because of the compaction of the packing of the particles in the direction of the spinal column, said shrinkage exerting dangerous forces on the injured spinal column.

SUMMARY OF THE INVENTION

It is accordingly an object of the invention to provide a device for supporting and stabilizing an injured person or injured body part and a corresponding production method, which overcomes the above-mentioned disadvantages of the heretofore-known devices and methods of this general type and which has a reduced shrinkage in length and an improved stability in the longitudinal and transverse directions.

With the foregoing and other objects in view there is provided, in accordance with the invention, a device for supporting and stabilizing an injured person or injured body part, comprising:

a flexible film element to be secured to the injured person or body part and enclosing an airtight evacuable inner space;

two insert bodies disposed in said inner space, said insert bodies lying on one another and each being formed from two air-permeable, flexible lengths of material;

a plurality of seams dividing each of said insert bodies into a plurality of chambers each containing loose particles;

said seams on each one of said insert bodies intersecting one another and forming a respective grid of seams, and said grids of seams on said two insert bodies being offset with respect to one another such that said particles complement one another to form a substantially uniformly thick layer of particles.

This is achieved in that the seams on each insert body intersect one another, and the seams of the first insert body are offset with respect to those of the second. This avoids chambers which are continuous in all directions, and the iimbricated overlapping of the chambers ensures the stability of the evacuated device in the longitudinal and transverse directions. The mutually intersecting seams likewise bring about a substantial reduction in the shrinkage in these two directions, since the length and width of the chambers are small.

In particular, the seams intersect one another at right angles, but could also form triangles in each case. The grids of seams are preferably offset in such a manner that each intersecting point of the seams on one insert body lies in the center of a grid area, which is formed by the seams, on the second insert body.

In a further preferred embodiment with seams intersecting one another at right angles, provision is made for the length and the width of each insert body to be divided into an uneven number of units, and for the distance between two seams to correspond in each case to two units, an outermost seam in each case on the two insert bodies being one unit away from the edge. In this manner, a non-centered grid of seams is obtained permitting two identical insert bodies to be provided, one of the two insert bodies being arranged rotated through 180° in the plane.

A second embodiment of the configuration makes provision for the length and the width of each insert body to be divided into an even number of units, and for the distance between two seams to correspond in each case to two units, all of the outermost seams on one insert body each being one unit, and on the other insert body, each being two units, away from the edge. Two insert bodies which are taken in to different extents and which both have centered grids of seams are provided here, one insert body having smaller edge chambers throughout.

In both cases, the two insert bodies are placed one on the other in a covering manner, and each intersecting point of seams of one insert body lies in the center of an area, which is bounded by the seams, of the other insert body.

With the above and other objects in view there is also provided, in accordance with the invention, a method for producing an insert body for a device for supporting and stabilizing an injured person or injured body part by way of a flexible film element to be secured around the injured person or body part and encloses an airtight evacuable inner space. The novel method comprises:

connecting two air-permeable, flexible lengths of material to one another on two mutually opposite first edges, by way of first seams extending parallel to the first edges, and on one of two second edges to thereby form channels;

alternately filling the channels with particles and dividing the channels into chambers by forming second seams extending parallel to the first second edge, and continuing the filling and forming steps until a second second edge is reached.

In other words, an insert body of this type can be produced by two air-permeable, flexible lengths of material being connected to each other on two mutually opposite first edges, by means of first seams parallel to the by edges, and on one of the two second edges, and by the channels which are formed being alternately filled with particles and, by means of second seams which are parallel to the first second edge, being divided into chambers until the second second edge is reached.

Other features which are considered as characteristic for the invention are set forth in the appended claims.

Although the invention is illustrated and described herein as embodied in a device for supporting and stabilizing an injured person or injured body part and method for producing it, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
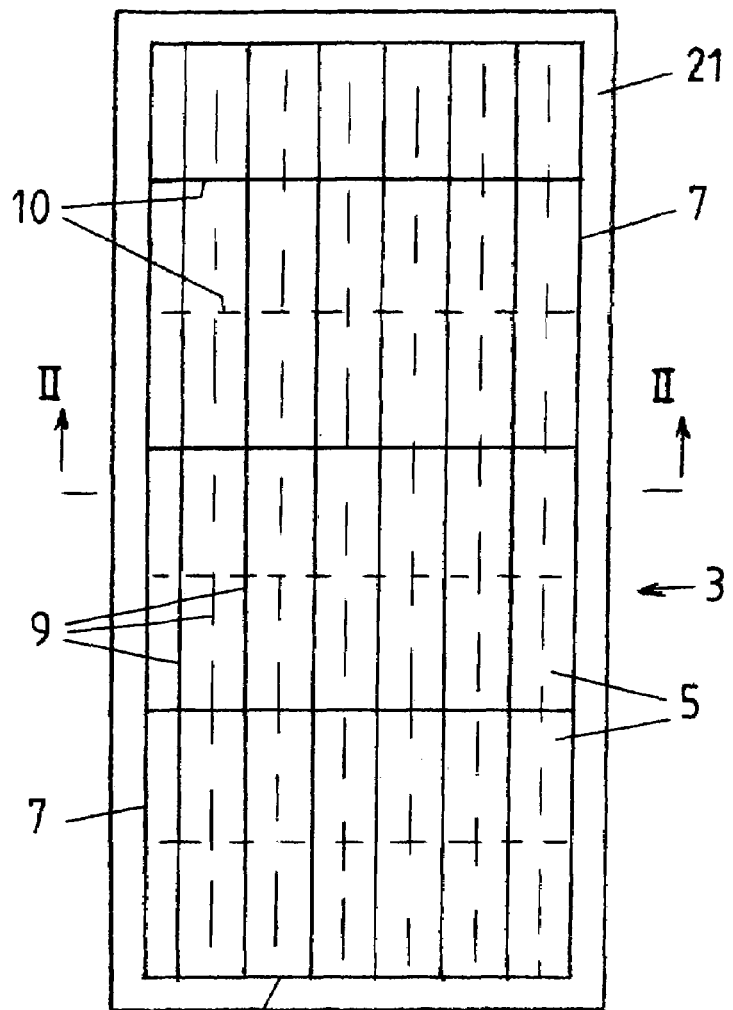
FIG. 1 is a schematic plan view of a first embodiment of a device according to the invention without a covering film.
Figure 2:
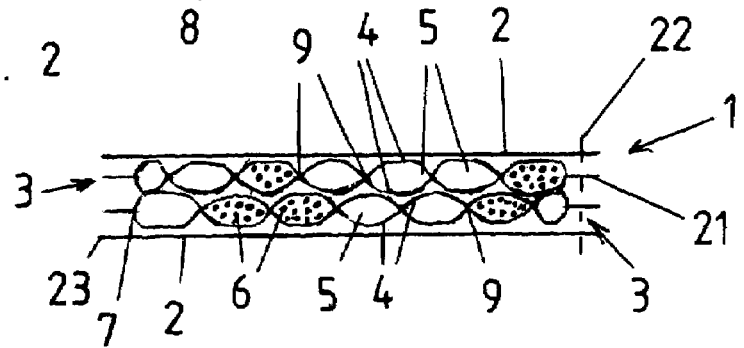
FIG. 2 is a section taken along the line II-II in FIG. 1.
Figure 4:
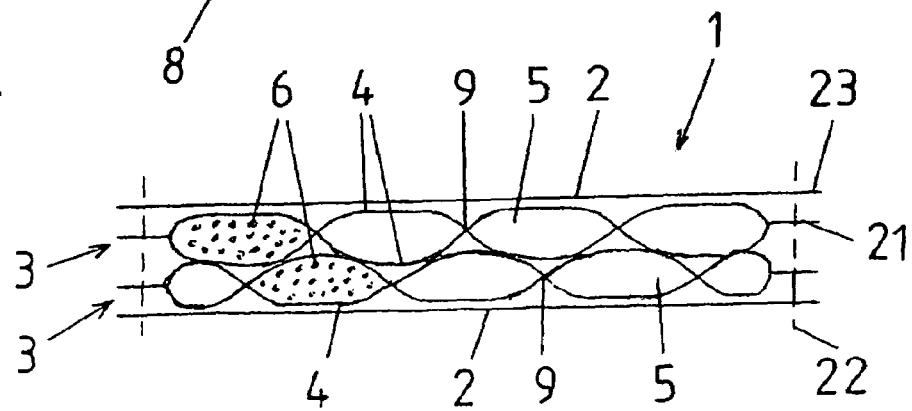
FIG. 4 is a section taken along the line IV-IV in FIG. 3.

Referring now to the figures of the drawing in detail and first, particularly, to FIG. 1 thereof, there is shown an assembly for stabilizing and supporting an injured person with a film element 1 which is composed of two airtight films 2 which consist, for example, of polyvinyl chloride or polyurethane. The two films are welded to each other along their edges 23. The weld is indicated in FIGS. 2 and 4 by the dashed lines 22 for reasons of clarity. The film 2 which will bear on the injured person is smooth, and a non-illustrated stiffening film piece on which inlet and outlet slits for fastening straps are provided can be fixed on the outer film 2, if the latter consists of polyurethane. As an alternative, for the fixing of the fastening straps film strips, in which eyelets having a central web are arranged, may be attached to the outer film 2. A valve is arranged in the outer film 2 and can be used to suck out air from the inner space containing a bulk mass of particles 6, for example plastic beads, made from foamed polystyrene or foamed polypropylene. The film element 1, which is soft and flat prior to use, is drawn up from the flat state around the injured person and is fixed with the aid of the straps to the head, trunk and thighs, for example. If the air is now sucked out, the film element stiffens in the configuration which is matched to the body shape, since the particles 6 lose their freedom of movement and they are pressed against one another by the outer air pressure.

The inner space is divided by four flexible, air-permeable lengths of material 4, an insert body 3, in which the particles 6 are contained in chambers 5, being formed from two lengths of material 4 in each case. The chambers 5 are bounded by mutually intersecting seams 9, 10 which connect the two lengths of material 4 of each of the two insert bodies 3. An encircling edge strip 21 of each insert body 3 serves the fixing between the two films 2. The air-permeable lengths of material 4 are preferably produced from a woven fabric of polypropylene fibers. The two insert bodies 3 are arranged in such a manner that the mutually intersecting seams 9 and 10 are offset in each case by half the distance both in the longitudinal direction and in the transverse direction. The seams 9, 10 of the lower insert body 3 are illustrated by dashed lines. As can be seen from FIGS. 2 and 4, the center or the apex of each chamber 5 lies above an intersecting point of the seams 9, 10 of the lower insert body 3. The height of the particle filling in the two insert bodies 3 is therefore substantially equalized, since there is a maximum amount in each apex of a chamber 5 above each intersecting point of the seams, in which there are no particles.

In the embodiment according to FIGS. 1 and 2, two identical insert bodies 3 can be used if their length and their width are divided into an identical or different uneven number of units, for example 7 length units and 13 width units, and the distance between two seams 9 and 10 is in each case two of the corresponding units. Owing to the uneven number of units, one of the two seams 9 is inevitably at the distance of one width unit from the longitudinal edge 7, and the second is at the distance of two width units from the other longitudinal edge 7. The same applies to the seams 10, the outermost of which are one or two length units away from the transverse edges 8. One insert body 3 is rotated through 180° in the plane (or turned about its longitudinal and its transverse center axis), as a result of which the arrangement of offset seams shown in FIG. 1 is obtained.

Figure 3:
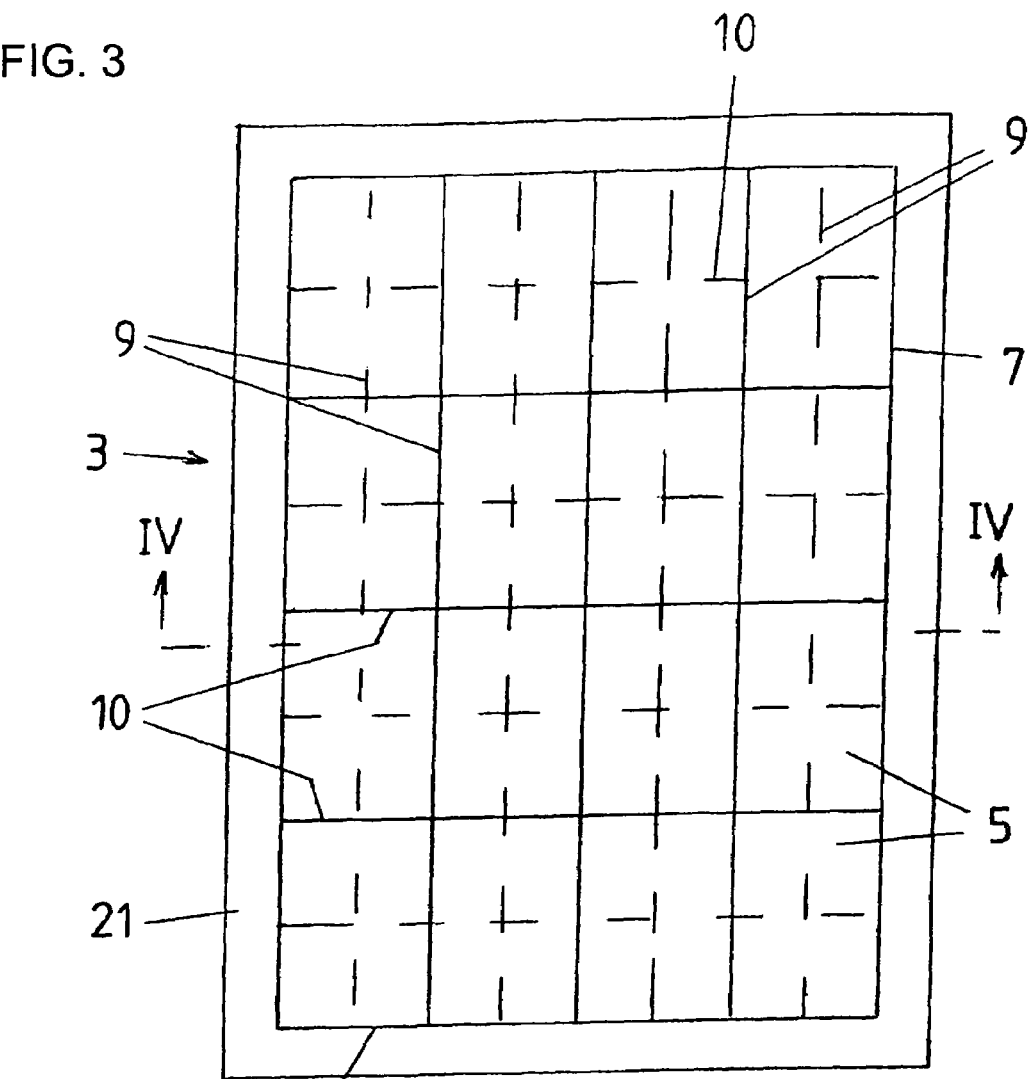
FIG. 3 is a schematic plan view of a second embodiment, likewise without a covering film.

In the embodiment according to FIGS. 3 and 4, two insert bodies stitched differently are provided, the length and width being divided into an even number of units, for example 8 in each case. The distance between the seams 9 or 10 is again two length or two width units. The distances of the outermost seams 9, 10 from the longitudinal and transverse edges 7 and 8 differ being two units in each case in the insert bodies 3 which can be seen in FIG. 3 and being one unit throughout in each case in the lower insert bodies 3.

The production of an insert body 3 takes place in particular in such a manner that two lengths of material 4 of corresponding size are connected to each other along their first (longitudinal) edges 7 and along a second (transverse) edge 8, and are divided into channels by means of the (longitudinal) seams 9. Particles 6 are then introduced up to a predetermined height (two units) and a (transverse) seam 10 is made. After the next filling, the next (transverse) seam is produced, etc. until the other (transverse) edge 8 is reached.

Two insert bodies 3 are placed one above the other on a film 2 and are welded together to the latter and a covering film 2 along the edge strips 21, 23.

I claim:
1. A device for supporting and stabilizing an injured person or injured body part, comprising:
   a flexible film element to be secured to the injured person or body part and enclosing an airtight evacuable inner space;
   two insert bodies disposed in said inner space, said insert bodies lying on one another and each being formed from two air-permeable, flexible lengths of material;
   a plurality of seams dividing each of said insert bodies into a plurality of chambers each containing loose particles;
   said seams on each one of said insert bodies intersecting one another and forming a respective grid of seams, and said grids of seams on said two insert bodies being offset with respect to one another such that said particles complement one another to form a substantially uniformly thick layer of particles.

2. The device according to claim 1, wherein said seams form a rectangular grid with said seams intersecting one another substantially at right angles.

3. The device according to claim 2, wherein a length and a width of each insert body are divided into an uneven number of units, and a distance between two respective said seams corresponds in each case to two units, an outermost seam in each case on said two insert bodies being spaced from an edge of said insert body by one unit.

4. The device according to claim 2, wherein a length and a width of each insert body are divided into an even number of units, and a distance between two respective said seams corresponds in each case to two units, and all outermost seams on one insert body are spaced from an edge thereof by one unit, and all outermost seams on the other insert body are spaced from an edge thereof by two units.

5. The device according to claim 1, wherein said two grids of seams are offset relative to one another such that each intersecting point of said seams on one insert body lies substantially in a center of a grid area formed between said seams on the respectively other said insert body.

* * * * *